US011480555B2

(12) United States Patent
Potyrailo et al.

(10) Patent No.: US 11,480,555 B2
(45) Date of Patent: Oct. 25, 2022

(54) SENSING SYSTEM AND METHOD

(71) Applicant: General Electric Company, Schenectady, NY (US)

(72) Inventors: Radislav Alexandrovich Potyrailo, Niskayuna, NY (US); Richard St. Pierre, Niskayuna, NY (US); Emad Andarawis Andarawis, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 595 days.

(21) Appl. No.: 16/412,497

(22) Filed: May 15, 2019

(65) Prior Publication Data
US 2021/0063366 A1 Mar. 4, 2021

(51) Int. Cl.
*G01N 33/00* (2006.01)
*G01N 33/52* (2006.01)

(52) U.S. Cl.
CPC ..... *G01N 33/0011* (2013.01); *G01N 33/0031* (2013.01); *G01N 33/0036* (2013.01); *G01N 33/0062* (2013.01); *G01N 33/521* (2013.01)

(58) Field of Classification Search
CPC ........................................ G01N 33/0004–0075
See application file for complete search history.

(56) References Cited

U.S. PATENT DOCUMENTS

| | | | |
|---|---|---|---|
| 6,560,471 B1 | 5/2003 | Heller et al. | |
| 6,589,438 B2 | 7/2003 | Bright et al. | |
| 7,062,385 B2 | 6/2006 | White et al. | |
| 7,319,411 B2 | 1/2008 | Ong et al. | |
| 7,763,208 B2 * | 7/2010 | Steichen | G01N 33/0031 422/88 |
| 8,323,982 B2 | 12/2012 | Leboeuf et al. | |
| 8,836,520 B1 * | 9/2014 | Crook | G01N 33/0044 340/630 |
| 9,366,664 B2 | 6/2016 | Anglin et al. | |

(Continued)

OTHER PUBLICATIONS

J.A. Paradiso et al., "Energy scavenging for mobile and wireless electronics", IEEE Pervasive Computing, vol. No. 04, Issue:01, pp. 18-27, Jan.-Mar. 2005.

(Continued)

*Primary Examiner* — Alexander A Mercado
(74) *Attorney, Agent, or Firm* — Armstrong Teasdale LLP

(57) ABSTRACT

A sensor system includes an electrical circuit having plural leads coupled with one or more sensing regions. The sensing regions include gaps having sensing materials that detect an analyte of interest. The gaps close responsive to the sensing material corresponding to the gaps detecting the analyte of interest. One or more processors communicatively coupled with the electrical circuit receive electrical signals from the electrical circuit indicative of the gaps closing responsive to the sensing material of the corresponding gaps detecting the analyte of interest. The electrical circuit is in a closed position in the presence of the analyte of interest. The sensor system is configured to consume an increased amount of power when the electrical circuit is in the closed position relative to the electrical circuit in an open position responsive to the one or more of the gaps closing. A responsive action is determined based on the electrical signals.

23 Claims, 6 Drawing Sheets

(56) References Cited

U.S. PATENT DOCUMENTS

| | | | | |
|---|---|---|---|---|
| 10,718,711 | B1* | 7/2020 | Guo | G01N 33/005 |
| 2009/0278685 | A1* | 11/2009 | Potyrailo | G01N 33/0006 |
| | | | | 340/572.1 |
| 2011/0101996 | A1* | 5/2011 | Potyrailo | G01D 21/00 |
| | | | | 324/655 |
| 2012/0001730 | A1* | 1/2012 | Potyrailo | G06K 19/0717 |
| | | | | 340/10.1 |
| 2016/0334353 | A1* | 11/2016 | Potyrailo | G02B 6/00 |
| 2017/0138922 | A1* | 5/2017 | Potyrailo | G01M 13/021 |
| 2017/0187541 | A1* | 6/2017 | Sundaresan | G01N 27/00 |
| 2017/0336378 | A1* | 11/2017 | Kim | G01N 33/0063 |
| 2018/0080890 | A1* | 3/2018 | Potyrailo | H04Q 9/00 |
| 2018/0080891 | A1* | 3/2018 | Potyrailo | G01N 33/0036 |
| 2018/0231514 | A1* | 8/2018 | Kim | G01N 27/021 |
| 2019/0369075 | A1* | 12/2019 | Schwartz | G01N 27/127 |
| 2020/0116694 | A1* | 4/2020 | Rinaldi | G01N 27/12 |
| 2021/0104140 | A1* | 4/2021 | Park | G05B 15/02 |

OTHER PUBLICATIONS

Potyrailo et al., "Materials and Transducers Toward Selective Wireless Gas Sensing", Chem Rev, vol. No. 111, Issue: 11, pp. 7315-7354, Nov. 9, 2011.

Zhou et al., "Harvesting Ambient Environmental Energy for Wireless Sensor Networks: A Survey", Journal of Sensors 2014, vol. No. 2014, Issue: 815467, Jun. 12, 2014.

Potyrailo et al., "Multivariable Sensors for Ubiquitous Monitoring of Gases in the Era of Internet of Things and Industrial Internet", Chem. Rev. 2016, vol. No. 116, Issue:19, pp. 11877-11923, Sep. 7, 2016.

Rudiger et al., "Real-Time Performance of a Self-Powered Environmental IoT Sensor Network System", Sensors, vol. 17, Issue:2, p. 282, Feb. 2017.

V. Rajaram et al., "Microelectromechanical detector of infrared spectral signatures with near-zero standby power consumption", 2017 19th International Conference on Solid-State Sensors, Actuators and Microsystems (Transducers), Kaohsiung, pp. 846-849, Jun. 18-22, 2017.

Mukherjee et al., "Sleep Scheduling in Industrial Wireless Sensor Networks for Toxic Gas Monitoring", IEEE Wireless Communications, vol. No. 24, Issue: 04, pp. 106-112, Aug. 2017.

Qian et al., "Zero-power infrared digitizers based on plasmonically enhanced micromechanical photoswitches", Nature Nanotechnology, vol. No. 12, pp. 969-973, Sep. 11, 2017.

Babayo et al., "A Review on energy management schemes in energy harvesting wireless sensor networks", Renewable and Sustainable Energy Reviews, vol. No. 76, pp. 1176-1184, Sep. 2017.

Akbari et al., "A Multisource Energy Harvesting Platform for Wireless Methane Sensor", Advances in Network Systems: Architectures, Security, and Applications, pp. 337-350, Dec. 2017.

Baranov et al., "Feasibility of RF energy harvesting for wireless gas sensor nodes", Sensors and Actuators A: Physical, vol. No. 275, Issue: 1, pp. 37-43, Jun. 2018.

Wang et al., "A Battery-Powered Wireless Ion Sensing System Consuming 5.5 nW of Average Power", IEEE Journal of Solid-State Circuits, vol. No. 53, Issue: 07, Jul. 2018.

Wu et al., "WE-Safe: A wearable IoT sensor node for safety applications via LoRa", 2018 IEEE 4th World Forum on Internet of Things (WF-IoT), Singapore, pp. 144-148, 2018.

V.Rajaram et al., "MEMS-based near-zero power infrared wireless sensor node", 2018 IEEE Micro Electro Mechanical Systems (MEMS), Belfast, pp. 17-20, 2018.

* cited by examiner

SENSING SYSTEM AND METHOD

FIELD

One or more embodiments are disclosed that relate to systems and methods for sensing gases.

BACKGROUND

Conventional gas sensors that operate for extended periods of time struggle to provide reliable and accurate information about gas composition in diverse applications ranging from industrial safety, environmental surveillance, medical diagnostics, or homeland security. Often these sensors are deployed as small form factor systems that have minimal available power either through the use of a battery or energy harvesting. These gas sensors operate and consume power even without the presence of gas analytes of interest, and eventually require manual re-charging that can include labor-intensive visits if the sensors are positioned in remote locations for unattended operation.

BRIEF DESCRIPTION

In one or more embodiments, a sensor system includes an electrical circuit having plural leads operably coupled with one or more sensing regions. One or more of the sensing regions includes a gap having a sensing material. The sensing material of each of the sensing regions is configured to detect an analyte of interest. One or more of the gaps is configured to close responsive to the sensing material corresponding to the one or more gaps detecting the analyte of interest. The sensor system also includes one or more processors communicatively coupled with the electrical circuit. The one or more processors receive one or more electrical signals from the electrical circuit indicative of one or more of the gaps closing responsive to the sensing material of the corresponding gaps detecting the analyte of interest. The electrical circuit is in a closed position in the presence of the analyte of interest. The sensor system is configured to consume an increased amount of power when the electrical circuit is in the closed position relative to the electrical circuit in an open position responsive to the one or more of the gaps closing. The one or more processors are configured to determine a responsive action based on the one or more electrical signals.

In another embodiment, a method includes detecting an analyte of interest with sensing material of one or more sensing regions of an electrical circuit of a sensor system. One or more of the sensing regions includes a gap comprising the sensing material. One or more of the gaps are configured to close responsive to the sensing material corresponding to the one or more gaps detecting the analyte of interest. The sensor system is configured to consume an increased amount of power when the electrical circuit is in a closed position relative to the electrical circuit in an open position responsive to the one or more of the gaps closing. One or more electrical signals are received from the electrical circuit indicative of one or more of the gaps closing responsive to the sensing material of the corresponding gaps detecting the analyte of interest. A responsive action is determined based on the one or more electrical signals.

In another embodiment, a sensor system includes an electrical circuit comprising plural leads operably coupled with one or more sensing regions. One or more of the sensing regions includes a gap comprising a sensing material. The sensing material of each of the sensing regions is configured to detect an analyte of interest. One or more of the gaps are configured to close responsive to the sensing material corresponding to the gaps detecting the analyte of interest. One or more processors are communicatively coupled with the electrical circuit. The one or more processors are configured to receive one or more electrical signals from the electrical circuit indicative of one or more of the gaps closing responsive to the sensing material of the corresponding gaps detecting the analyte of interest. The one or more gaps are configured to close responsive to a ratio between a real part of a complex permittivity of the sensing material and an imaginary part of the complex permittivity of the sensing material exceeding at least one predetermined threshold. The one or more processors are configured to determine a responsive action based one the one or more electrical signals.

In another embodiment, a method includes detecting an analyte of interest with sensing material of one or more sensing regions of an electrical circuit of a sensor system. One or more of the sensing regions includes a gap comprising the sensing material. One or more of the gaps are configured to close responsive to the sensing material corresponding to the gaps detecting the analyte of interest. The one or more gaps are configured to close responsive to a relationship between a real part of a complex permittivity of the sensing material and an imaginary part of the complex permittivity of the sensing material exceeding a predetermined threshold. One or more electrical signals are received from the electrical circuit indicative of one or more of the gaps closing responsive to the sensing material of the corresponding gaps detecting the analyte of interest. A responsive action is determined based on the one or more electrical signals.

DETAILED DESCRIPTION

Figure 1:
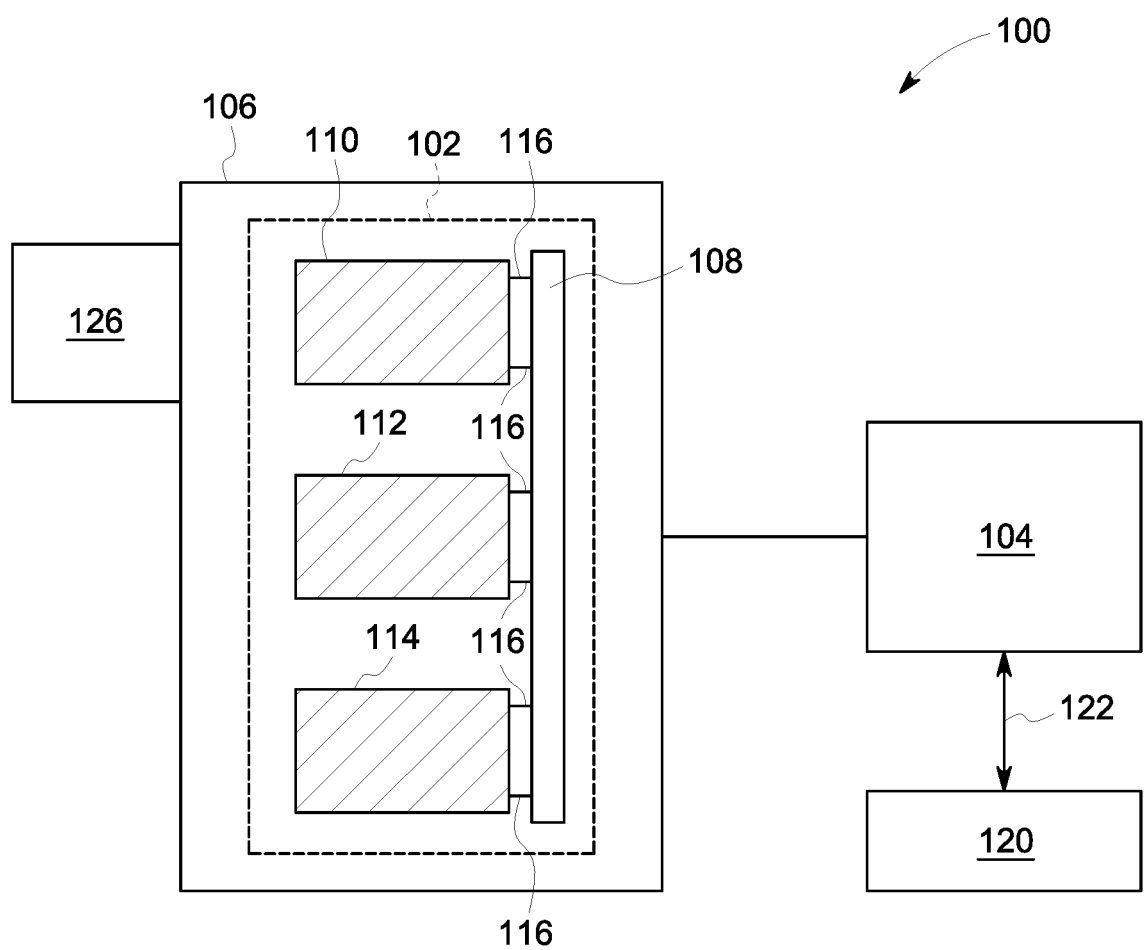
FIG. 1 illustrates one embodiment of a sensor system in accordance with one embodiment.

One or more embodiments of the inventive subject matter described herein include sensor systems and methods that provide a reliable operation of a gas detector system that operates with zero standby power. A circuit system of the sensor system includes an electrical circuit operably coupled with one or more sensing regions having sensing materials. The circuit system is in an initial or normal standby-state or open position. Responsive to certain types of analytes of interest coming into contact with one or more of the sensing regions, a gap of the sensing region may close and change the state of the circuit system from the normal open position to a closed position (e.g., an on-mode or active state). When the sensor system is turned on responsive to the circuit system changing from the open position to the closed position, a sensor response is produced and transmitted wirelessly to a receiver. The receiver may be positioned anywhere geographically relative to the sensor system, and may be associated with any number of sensor systems.

The sensing system may be in an open position in the absence of the analyte of interest, and may be in a closed position in the presence of the analyte of interest. The sensor system is configured to consume an increased amount of power when the circuit system is in the closed position relative to when the circuit system is in the open position.

The one or more processors of the sensor system receive an electrical signal from the circuit system indicative of one of the gaps closing responsive to the sensing material detecting the analyte of interest. The electrical signal may include one or more properties of the electrical signal, an identification of the detected analyte of interest, a quantitative amount of the analyte of interest detected, or the like. Responsive to receiving the electrical signal from the circuit system, the one or more processors determine a responsive action based on the electrical signal. For example, the responsive action may include a direction to a user or subject of the sensor system, may include a direction to an asset of the subject, or any combination therein.

At least one technical effect of the various embodiments herein includes a sensor system that consumes an amount of power when the sensor system is in the open position (e.g., the off-mode) relative to an amount of power when the sensor system is in the closed position (e.g., the on-mode). The sensor system changes between the off-mode and the on-mode responsive to one or more sensing regions having a sensing material detect an analyte of interest. As another technical effect, the circuit system includes logic circuitry for sensor accuracy of the gas sensing in the presence of numerous interferences or interfering fluids. For example, the sensor system having plural sensing regions can include sensor logic patterns for the sensor to change from the normal open position (e.g., off-mode) to the closed position (e.g., on-mode). Changing the state of the sensor system changes an amount of power consumed by the sensor system between when the sensor system is in the off-mode and when the sensor system is in the on-mode.

FIG. 1 illustrates one embodiment of a sensor system 100 in accordance with one embodiment. The sensor system 100 includes a circuit system 102 that includes and/or is operably coupled with a sensor 106. The sensor system 100 also includes a power source 126 that can supply or provide power to the circuit system 102 using energy available from a main system (e.g., a battery, alternating current, or the like), or by using harvesting of energy from ambient sources (e.g., light, vibration, heat, electromagnetic energy, or the like).

The circuit system 102 includes an electrical circuit 108 having plural leads 116 that are operably coupled with one or more sensing regions 110, 112, 114. In the illustrated embodiment of FIG. 1, the system 102 includes three sensing regions 110, 112, 114, however in alternative embodiments the system 102 may include less than three or more than three different sensing regions. Each of the sensing regions 110, 112, 114 include transducers. The sensing regions 110, 112, 114, and the transducers will be described in more detail below with reference to FIGS. 2, 3, and 4. In one or more embodiments, the electrical circuit 108 may include components for dual detection configuration (e.g., to detect increasing values of gas concentrations and/or decreasing values of gas concentrations). Optionally, the electrical circuit 108 can include protection circuit elements, such as Zener diodes, capacitors, controllers, or the like, to address voltage excursions, handling, external noise sources, or the like.

The circuit system 102 is coupled with a system controller 104. The system controller 104 may include one or more processors for analyzing data received from the electrical circuit 108. For example, the one or more processors may be one or more of computer processors, controllers (e.g., microcontrollers), or other logic-based devices that perform operations based on one or more sets of instructions (e.g., software). The instructions on which the one or more processors operation may be stored on a tangible and non-transitory computer readable storage medium, such as a memory device that may include a hard drive, a flash drive, RAM, ROM, EEPROM, and/or the like. Additionally or alternatively, one or more of the sets of instructions that direct operations of the one or more processors may be hard-wired into the logic of the one or more processors, such as by being hard-wired logic formed and/or stored in the hardware of the one or more processors.

In the illustrated embodiment of FIG. 1, the system controller 104 is illustrated in a separate housing or unit than the circuit system 102. Alternatively, the system controller 104 may be disposed within a common housing or common structure with the circuit system 102 including the electrical circuit 108 and the sensing regions 110, 112, 114.

The sensor system 100 can also include a remote central station 120. The remote central station 120 may be disposed within a common facility, structure, warehouse, or the like, as the circuit system 102, may be disposed several kilometers away from the circuit system 102, or the like. For example, the circuit system 102 and the system controller 104 may be disposed in one room of a building and the central station 120 may be disposed in a different room of a building. Optionally, the circuit system 102 and the system controller 104 may be disposed in one geographical area, and the central station may be disposed in a different geographical area separated from the first geographical area by plural feet, miles, kilometers, or the like. The central station 120 may be communicatively coupled with the system controller 104 via one or more bi-directional communication links 122 (e.g., enabling wired and/or wireless communication via a satellite, cellular tower, or the like). Optionally, the central station 120 may be communicatively coupled with the circuit system 102 via one or more alternative bi-directional communication links. The system controller 104 and/or the circuit system 102 may communicate electrical signals with the central station 120.

In one or more embodiments, the sensor 106 and/or the circuit system 102 is a first sensor or circuit system, respectively. The central station 120 may be communicatively coupled with the first sensor and one or more different sensors and one or more different circuit systems. For example, the first sensor 106 and first circuit system 102 may be disposed in a first geographical location and the second sensor and second circuit system (not shown) may be disposed in a different geographical location. The central station 120 may be communicatively coupled with each sensor and/or each circuit system 102, each sensor may be communicatively coupled with each other sensor, each circuit system may be communicatively coupled with each other circuit system, or any combination therein.

Figure 2:
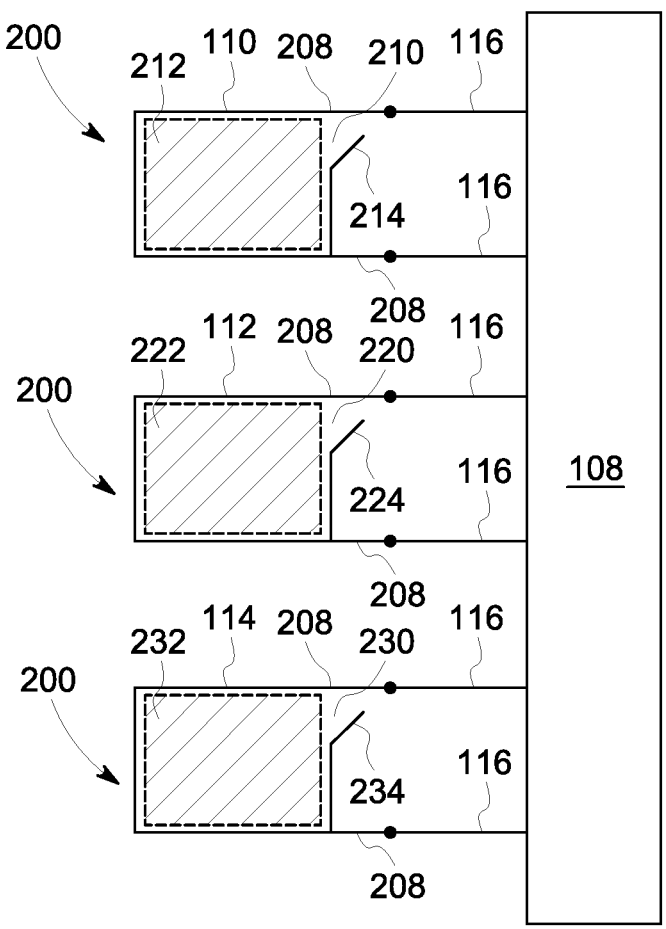
FIG. 2 illustrates sensing regions of the sensor system shown in FIG. 1 in accordance with one embodiment.

FIG. 2 illustrates the sensing regions 110, 112, 114 of the sensor system 100 in accordance with one embodiment. The electrical circuit 108 includes the plural leads 116 that are coupled with leads 208 corresponding to each of the sensing regions 110, 112, 114. The sensing regions 110, 112, 114 may be combined or electrically coupled with each other sensing region 110, 112, 114 in series, in parallel, in a combination of series and/or parallel, or any combination therein.

Transducers 200 of each of the sensing regions 110, 112, 114 includes a gap 210, 220, 230 and a sensing material 212, 222, 232, respectively. The gaps 210, 220, 230 can be geometrical and/or non-geometrical non-conductive gaps of the electrical circuit 108. The non-conductive gaps are filled or substantially filled with the corresponding sensing materials. The sensing material may be a semiconductor material or a metal oxide material. Optionally, the sensing material of each of the sensing regions 110, 112, 114 may be a common sensing material or one or more sensing regions may include a unique sensing material relative to the sensing material of each other sensing region. The sensing materials may include polyaniline, ligand-functionalized metal nanoparticles, polymers with ionic properties, conducting polymers, conjugated polymers, ionic liquids, metallic nanotubes, carbon nanotubes, microwires, nanowires, or the like. The sensing materials 212, 222, 232 can have different responses of real and/or imaginary parts of the complex permittivity to different analyte species.

The sensing materials 212, 222, 232 detect one or more analytes of interest. In one embodiment, the sensing materials 212, 222, 232 may detect common or different analytes of interest relative to each other sensing material 212, 222, 232. The analyte of interest may be detected as an external stimulus to the sensing material such as fluid, such as a gas, liquid, solid, particles, or the like. Each of the sensing regions 110, 112, 114 includes a switch 214, 224, 234 that can move between an open position to a closed position responsive to the sensing material of the corresponding sensing region detecting an analyte of interest. In the presence of at least one analyte of interest, the switches associated with one or more of the gaps 210, 220, 230 may close and change the electrical circuit 108 from an open position to a closed position.

In one or more embodiment, one or more of the sensing materials may be a multi-response sensing material that may sense, detect, respond to, or the like, two or more different analytes of interest. For example, the sensing material 212 of the first sensing region 110 may detect a first and a different second analyte of interest. In the presence of one of the first and/or second analytes of interest, the gap 210 of the sensing region 110 may close, and change the state of the electrical circuit 108 from an open position to a closed position. Optionally, in the presence of a predetermined amount of the first and/or second, the gap 210 may close and change the state of the electrical circuit 108 to the closed position.

In one or more embodiments, one or more properties of the sensing material 212, 222, 232 can change responsive to the sensing material detecting an analyte of interest. For example, a state of the sensing material may change (e.g., from a liquid state to a solid state or to a solid-liquid mixture), a distribution of particles of the sensing material may change, or the like.

The gaps 210, 220, 230, are in a normal open position when no analytes of interest are present, when analytes of interest are present but an amount of the analytes of interest has not reached a predetermined threshold, or the like. Alternatively, one or more of the gaps 210, 220, 230 may close responsive to the corresponding sensing material detecting one or more analytes of interest. Responsive to the external stimulus being applied to the sensing regions 110, 112, 114, electric current starts to flow or move through the sensing region 110, 112, 114. One or more of the predetermined threshold levels may be adaptable based on one or more external inputs and/or external stimuli to the sensor system. In one or more embodiments, the external stimulus or external input may include an instruction message received from the central station 120, or the like. Additionally or alternatively, the predetermined threshold levels may be based on an internal input. For example, the internal input may be a performance of a certain sensor system, such as ambient environmental conditions (e.g., temperature, humidity, or the like), previously measured and/or logged data trends, wake-up logs and/or history, wake-up frequency, changing performance over time due to possible aging of the sensor system, adaptation to different environments, or the like.

The electric current is converted to a voltage level, and one or more of the gaps 210, 220, 230 may close responsive to the voltage level meeting and/or exceeding an upper limit or lower limit of a predetermined threshold. Until the voltage level meets and/or exceeds the predetermined upper limit or lower limit threshold, no electric current flows or moves through the electrical circuit 108. For example, the gap 210 may change from the open position to the closed position responsive to the sensing material 212 of the sensing region 110 detecting a first analyte of interest. Additionally, the gap 210 may change from the closed position to the open position, or may remain in the open position, responsive to the sensing material 212 detecting a different, second analyte of interest.

In one or more embodiments, two different categories of techniques for altering the threshold can include altering the gap and/or altering the detection circuity of the electrical circuit 108. Techniques to alter the properties of the gap can include electrostatic techniques (e.g., by changing an overlap between electrodes, by changing a separation distance or space between electrodes, by altering the complex permittivity of the sensing material by using an electric field above a certain strength, by using a magnetic field above certain strength, or the like) and mechanical techniques (e.g., by-stable structures, shape memory alloy, control of a gas-sampling port, or the like). Techniques to alter the properties of the detection circuitry can include control of one or more active components of the electrical circuit 108 by modifying circuit configuration, circuit bias, or the like.

In one or more embodiments, one or more of the gaps 210, 220, 230 may change between the open position to the closed position responsive to a relationship between a real part of a complex permittivity of the sensing material and an imaginary part of the complex permittivity of the sensing material. For example, the relationship may be a ratio or a percentage of the real part to the imaginary part of the complex permittivity, a difference between the real part and the imaginary part, or the like. Optionally, one or more of the gaps 210, 220, 230 may close responsive to the relationship between the real part and the imaginary part of the complex permittivity of the sensing material of the respective sensing region meeting and/or exceeding at least one predetermined threshold.

Closing one or more of the gaps 210, 220, 230 closes the electrical circuit 108 and changes the state of the electrical circuit 108 from the normal open position to a closed position. For example, no electric current is conducted through the electrical circuit 108 when the electrical circuit 108 is in the open position. Alternatively, electric current does conduct through the electrical circuit 108 when the electrical circuit 108 is in the closed position. The electrical circuit 108 changes between the open position (e.g., indicative of the absence of an analyte of interest) and the closed position (e.g., indicative of the presence of an analyte of interest).

In one or more embodiments, the system controller 104 can determine a predetermined threshold for a number of gaps of the one or more sensing regions to close that changes the electrical circuit 108 between the normal open position and the closed position. For example, the electrical circuit 108 may change to the closed position from the open position responsive to a single gap closing, to two or more gaps of the sensing regions closing, or the like. Optionally, the electrical circuit 108 may include logic based electrical components or one or more processors that may direct the electrical circuit 108 to change between the open and closed positions based on the number of gaps closing, based on which of the gaps closes (e.g., one of the sensing regions may be identified as having greater importance than the other sensing regions), or the like.

In one or more embodiments, the one or more processors of the system controller 104 can determine a predetermined threshold amount of an analyte of interest that is to be present for one or more of the gaps to close. For example, the switches 214, 224, 234 of the gaps 210, 220, 230, respectively, may close responsive to one or more of the sensing materials 212, 222, 232 detecting an amount of an analyte of interest that meets and/or exceeds the predetermined threshold. The switches 214, 224, 234 may close responsive to the sensing materials 212, 222, 232 detecting an increasing amount of the analyte of interest and/or a decreasing amount of an analyte of interest. For example, responsive to the amount of the analyte of interest increasing to meet and/or exceed an upper limit of a predetermined threshold, one of the gaps may close to change the electrical circuit 108 from the open position to the closed position. In another example, responsive to the amount of the analyte of interest decreasing to meet and/or exceed a lower limit of a predetermined threshold, one of the gaps may close to change the electrical circuit 108 from the open position to the closed position.

In one or more embodiments, one or more of the sensing regions 110, 112, 114 may include subregions disposed within the regions (not shown). The sensing regions may include any number of subregions having any substantially uniform or unique shapes and/or sizes relative to each other subregion. Each of the subregions may be filled with or include different and/or common sensing materials. For example, a first subregion may include or be filled with a first sensing material and a second subregion may include or be filled with a second sensing material. The gap of the corresponding sensing region may close (e.g., become electrically conductive) based on a logic pattern of the first and/or second subregions detecting one or more analytes of interest. For example, different subregions of each of the sensing regions can change the electrical state of the electrical circuit 108 based on what fluid (e.g., gas, liquid, particles, or the like) is in the environment.

In one or more embodiments, the different sensing regions 110, 112, 114 may be scaled or assigned to achieve different weighting of the sensing process. For example, the first sensing region 110 may be scaled or weighed to be more sensitive to a first analyte of interest relative to the second sensing region 112. Optionally, two or more of the sensing regions 110, 112, 114 may be assigned and/or scaled to have substantially common weighting of the sensing process. Optionally, one of the sensing regions may have a weight or scale that is greater than or less than the other of the sensing regions.

The electrical circuit 108 and the circuit system 102 in the closed position consumes, utilizes, draws, or the like, an increased amount of power from the power source 126 relative to when the electrical circuit 108 and the circuit system 102 is in the open position. For example, when the electrical circuit 108 is in the open position, the sensor system 100 may be referred to as being in an off-state, stand-by mode, or the like. Additionally, when the electrical circuit 108 is in the closed position, the sensor system 100 may be referred to as being in an on-state, active-mode, or the like. Responsive to the electrical circuit 108 changing from the open position to the closed position in the presence of an analyte of interest, the circuit system 102 draws, utilizes consumes, or the like, an amount of power from the power system 126 that is greater than an amount of power that is drawn, consumed, utilized, or the like, when the electrical circuit 108 is in the open position. For example, closing the electrical circuit 108 by closing one or more of the gaps 210, 220, 230 in the presence of one or more of the analytes of interest increases an amount of power that is consumed or utilized by the circuit system 102 relative to the electrical circuit 108 in the open position.

Sensor logic is possible in at least two different implementations, such as at the sensor itself and at the output of the detector sensor system. In a first implementation, including the sensor logic at the sensor itself, the sensor logic can be implemented by combining materials in geometrical shapes by forming logical paths. Known logic functions can be implemented such as "AND", "OR", "NOT", and/or other known logical functions and/or combinations of known logical functions. In the second implementation, including the sensor logic at the output of the detector sensor system, the sensor logic can be implemented by combining detector system outputs. Two or more detector system outputs connected in parallel can perform the "OR" function. Alternatively, two or more detectors connected in series can perform the "AND" function. With the addition of an inverting stage, the "NOT", "NAND", "NOR", or other known logic functions can be configured.

In one embodiment, the sensor can operate in a charge accumulation and redistribution configuration where the analyte of interest can act on one or more sensor elements by either changing the dielectric properties of the sensor element, by changing the detection/dielectric gap of the sensor element, or the like. A detection event can result in a change of capacitance. A zero standby power detection circuit can be constructed by applying a DC voltage across the capacitor sensor element. A change in capacitance results in the flow of charges either into or out of the capacitor structure. In one embodiment, the charges produced by the change in capacitance are accumulated on an accumulating capacitor (not shown). As the charges accumulate through subsequent detections of the analyte of interest, the charge across the accumulating capacitor continues to accumulate resulting in an increase in the magnitude of the voltage on the accumulating capacitor. Responsive to a predetermined threshold of accumulated voltage being reached, the accumulated voltage reaches a threshold level sufficient to change the state of a monitoring circuit from an off-state to an on-state. In one embodiment, the accumulated voltage reaches a significant level to electrostatically trigger a micromechanical or a similar switch that wakes up the monitoring circuit. In another embodiment, the accumulated charges turn on an electric-field sensitive device (not shown), such as a MOSFET. In another embodiment, the gate capacitance of an electronics device (e.g., MOSFET) may act as the accumulating capacitor. In one configuration, a single analyte detection event can be sufficient to trigger and wakeup the monitoring circuit.

The analyte can act on the sensor element by modifying the dielectric properties, by modifying the dielectric geometry by acting on the dielectric gap (e.g., be expanding the gap, decreasing or squeezing the gap by applying pressure, or the like), or a sensor constructed with a changing dielectric gap can be constructed as a differential sensor to improve detection sensitivity and performing the dual action such as compression of one element and contraction of another element and reducing the error by providing a reference.

Figure 3:
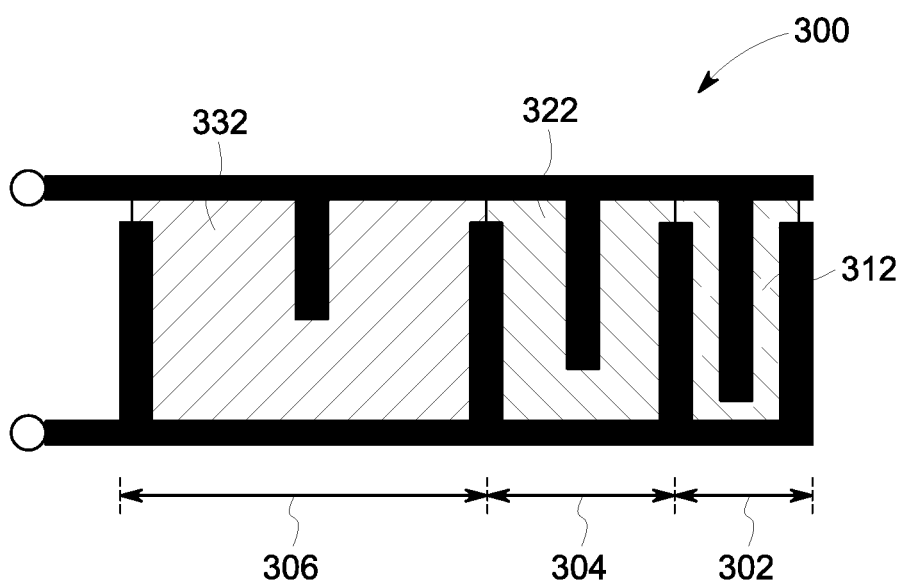
FIG. 3 illustrates a multiscale transducer in accordance with one embodiment.

FIG. 3 illustrates one example of a multiscale transducer in accordance with one embodiment. In one or more embodiments, one or more of the sensing regions 110, 112, 114 may include a multiscale transducer 300. In the illustrated embodiment of FIG. 3, the multiscale transducer 300 is in the form of an interdigital electrodes structure and accommodates three different sensing materials 312, 322, 332. The three different sensing materials allow the multi scale transducer 300 to produce different responses based on gaps 302, 304, 306 having different and/or substantially common widths or sizes. Additionally, each of the gaps 302, 304, 306 may be filled with or include a different sensing material relative to each other gap 302, 304, 306. In one or more embodiments, gaps having substantially common widths and/or sizes may include different sensing materials to produce a detectable signal change with an appropriate signal-to-noise performance. In one embodiment, one or more of the gaps 302, 304, 306 may be between about 1 nanometer (nm) and about 10 millimeters (mm). In another embodiment, one or more of the gaps 302, 304, 306 may be between about 5 nm and about 5 mm. In a more preferred embodiment, one or more of the gaps 302, 304, 306 may be between 10 nm and about 1 mm.

The sensing materials 312, 322, 332 may include materials such as polyaniline, ligand-functionalized metal nanoparticles, polymers having ionic properties, conducting polymers, conjugated polymers, ionic liquids, metallic nanotubes, carbon nanotubes, microwires, nanowires, or the like. In one or more embodiments, the multiscale transducer 300 may activate the electrical circuit 108 responsive to one of the sensing materials 312, 322, 332 detecting an analyte of interest. Optionally, the multiscale transducer 300 may activate the electrical circuit 108 responsive to each of the sensing materials 312, 322, 332 detecting one or more analytes of interest.

In one or more embodiments, the multiscale transducer 300 may include and/or accommodate plural different types of sensing materials to achieve different selectivity. For example, the different types of sensing materials may allow the multiscale transducer to detect or identify plural different analytes of interest. Optionally, in one or more embodiments, the multiscale transducer 300 may include and/or accommodate plural different types of sensing materials to achieve different sensitivity. For example, the multiscale transducer 300 may be more sensitive to the presence of one analyte of interest relative to a sensitivity of the multiscale transducer 300 to a different analyte of interest. Optionally, the multiscale transducer 300 may be more or less sensitive to one or more analytes of interest based on a predetermined threshold of an amount of a presence of the one or more analytes of interest.

Figure 4:
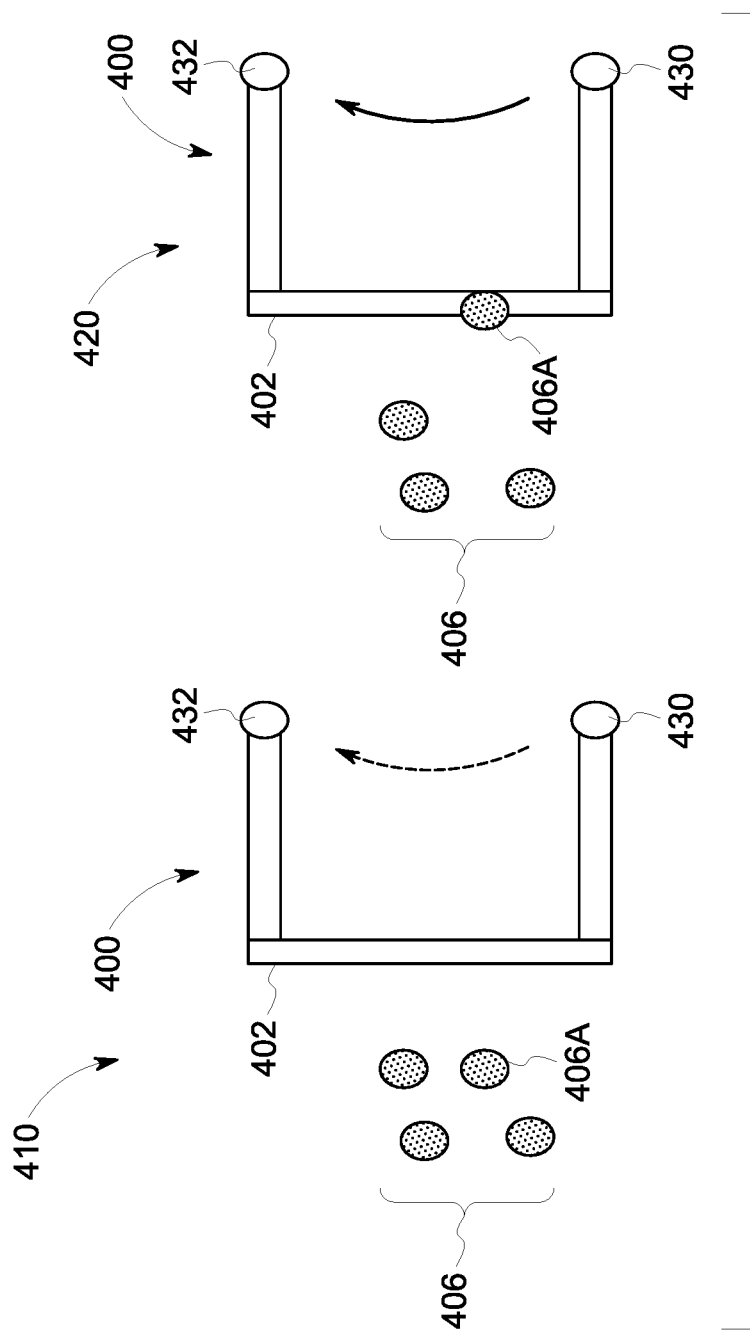
FIG. 4 illustrates a nanowire transducer in accordance with one embodiment.

In alternative embodiments, the transducer may serve or act as a sensing material for the logic circuitry of the electrical circuit 108. For example, FIG. 4 illustrates a nanowire transducer 400 in accordance with one embodiment. One or more of the sensing regions 110, 112, 114 may comprise a nanowire transducer 400. The nanowire transducer 400 includes a nanowire 402 that may be an environmentally sensitive single nanowire, for example produced by electrospinning of a conducting polymer. As shown at 410, the nanowire transducer 400 produces an open circuit in the absence of a fluid, such as a gas, liquid, or the like, having an analyte of interest. In the absence of the fluid, no current flows, passes through, or moves through leads 430, 432 and the nanowire transducer 400 is in an open state, an off-state, standby-state, or the like. Alternatively, when a single gas molecule 406A or two or more molecules 406 interact with the nanowire 402, the electric properties of the nanowire transducer 400 change by closing the circuit. For example, in the presence of at least one molecule of an analyte of interest, electric current flows, passes through, or moves through the leads 430, 432 and the nanowire transducer 400 is in a closed state, an on-state, or the like. Additionally or alternatively, the transducer may have any alternative configuration, and may include any number of nanowires that may detect the presence of one or more different analytes of interest.

Returning to FIGS. 1 and 2, in one or more embodiments, each of the sensing regions may be electrically connected with each other sensing region 110, 112, 114 in series, such that for the sensor 106 to conduct electric current through the electrical circuit 108, all sensing regions 110, 112, 114 must detect a presence of a gas and/or an analyte of interest. In one non-limiting example, a gas formulation of interest may be detected by each of the sensing regions 110, 112, 114 while an interfering gas may only be detectable by a subset of the sensing regions 110, 112, 114. The electrical circuit 108 will change from the open position to the closed position if all sensing regions 110, 112, 114 detect the presence of the gas of interest, and the interfering gas that is only detectable by the subset of the sensing regions (e.g., less than all of the sensing regions) will be rejected.

In one or more embodiments, scaling the sensitivity of each of the different gaps of the transducer achieves selectivity, rejects interference by interfering gases or fluids, and may include tuning to detect mixtures of two or more fluids, tuning to detect specific formulations, or the like, without expending energy. For example, until the transducers 200 and/or the multiscale transducers 300 detect an analyte of interest and the electrical circuit 108 changes from the open position to the closed position, the transducers 200 and/or the multiscale transducer 300 can be scaled to detect, reject, or the like, one or more analytes of interest while consuming a reduced amount of power relative to when the electrical circuit 108 changes to the closed position.

Optionally, scaling of the sensitivity of each of the different gaps enables sensor elements with different sensitivities to be achieved. High and/or low sensitivity sensors may be combined to enable certain sensor system responses. For example, in one embodiment, a sensor may be designed to exit the stand-by state, the zero-power state, or the like, and activate the electrical circuit 108 in a high concentration of a particular analyte of interest is detected, or if a low concentration of a combination of gases are achieved. For example, the system 100 may be sensitive to low levels of known combinations of gases (e.g., gases that are known to be precursors for explosives or drug manufacturing), while maintaining the ability to detect constituting elements at higher concentrations. Home-made explosives (HMEs) for improvised explosive devices (IEDs) are known to be made using available chemicals. Examples of volatile precursors of HMEs can include acetone, hydrogen peroxide, methyl ethyl ketone, toluene, sulfuric acid, and nitromethane. Volatile precursor chemicals for illegal drug manufacturing can include methylamine, phenylacetic acid, phenyl 2 propanone, and acetic acid. These and other relevant volatile precursor chemicals and the patterns of these chemicals can be detected using the sensor system described in this invention. This detection of the relevant volatile precursor chemicals and their patterns can be accomplished by the gas detection system that operates with zero standby power.

Responsive to one or more of the gaps 210, 220, 230 of the circuit system 102 changing between the open position and the closed position, and the electrical circuit 108 changing between an open position and a closed position, one or more electrical signals may be communicated from the electrical circuit 108 to the system controller 104. The electrical signals may include information such as one or more electrical properties, one or more characteristics of the electrical signals, identities of the one or more analytes of interest that may be detected by the one or more sensing regions, or the like.

Figure 5:
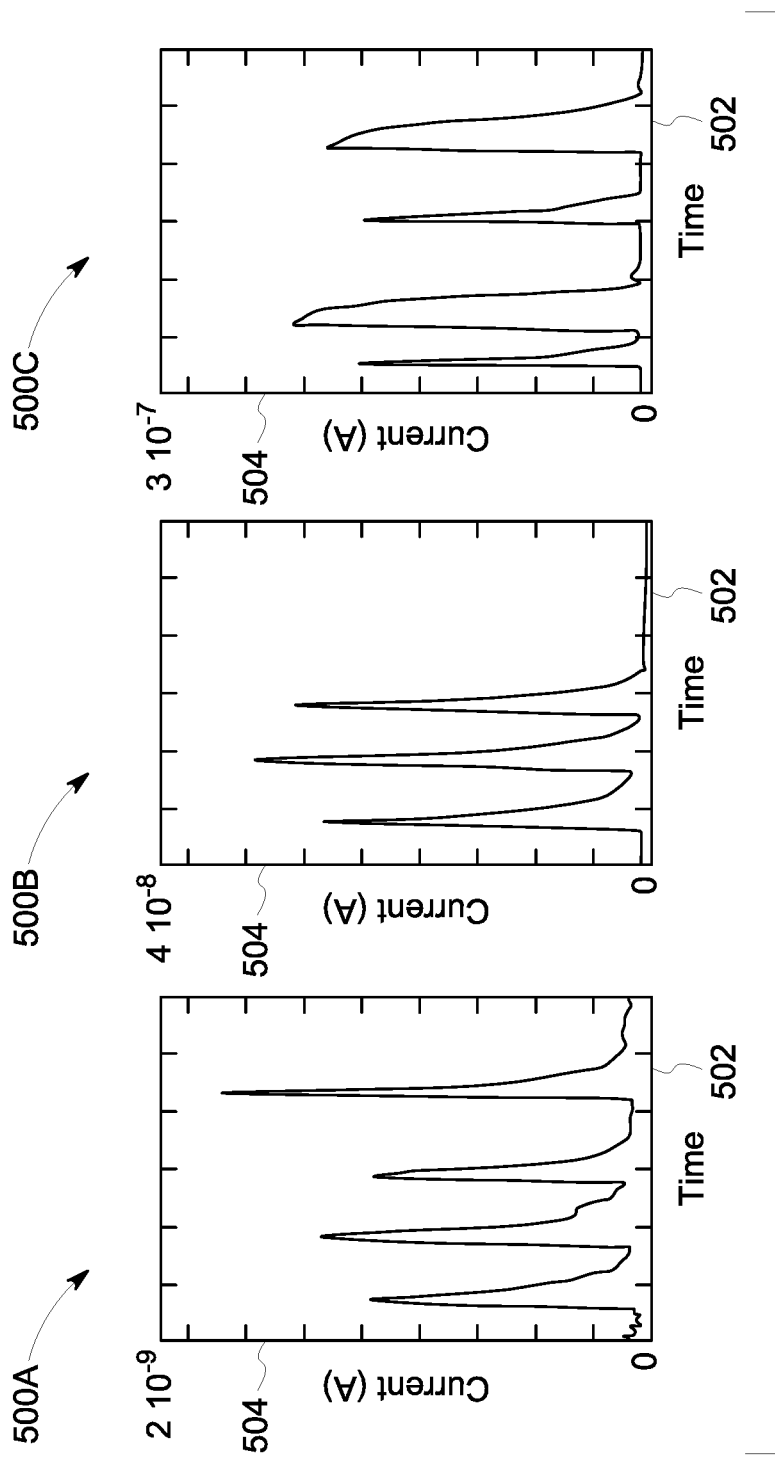
FIG. 5 illustrates graphical illustrations of current responses of a transducer of a sensor system in accordance with one embodiment.

FIG. 5 illustrates graphical illustrations of electric current responses of one of the transducers of the sensor system 100 in accordance with one embodiment. The graphs 500A, 500B, 500C are indicative of responses of one of the transducers of the circuit system 102 to different levels of a model gas. The model gas may be water vapor, toxic industrial chemical, chemical warfare agent in air, a volatile precursor of HMEs, a volatile precursor of illegal drug manufacturing, a pattern of one or more volatile precursors of HMEs, a pattern of one or more volatile precursors of illegal drug manufacturing, or an alternative fluid. In one embodiment, the transducers may be coated with a sensing material of an ionic polymer, optionally the sensing materials may be an alterative material such as polyaniline, metal oxide, or the like.

The electrical signals are shown alongside a horizontal axis 502 representative of time, and a vertical axis 504 representative of magnitudes of electric current. As initial state of the electrical circuit 108 is in a normal open position. For example, a reduced amount of electric current or substantially no electric current is present in the electrical circuit 108 when the electrical circuit 108 is in an initial state, standby-mode, off-mode, zero-power mode, or the like. Different levels of the model gas turn the electrical circuit 108 from the normal open position (e.g., the standby-mode or the off-mode) to the closed position (e.g., the on-mode) at different levels of electric current. For example, graph 500A produces about $10^{-9}$ amps of electric current, graph 500B produces about $10^{-8}$ amps of electric current, and graph 500C produces about $10^{-7}$ amps of electric current in the presence of the model gas (e.g., the analyte of interest).

Figure 6:
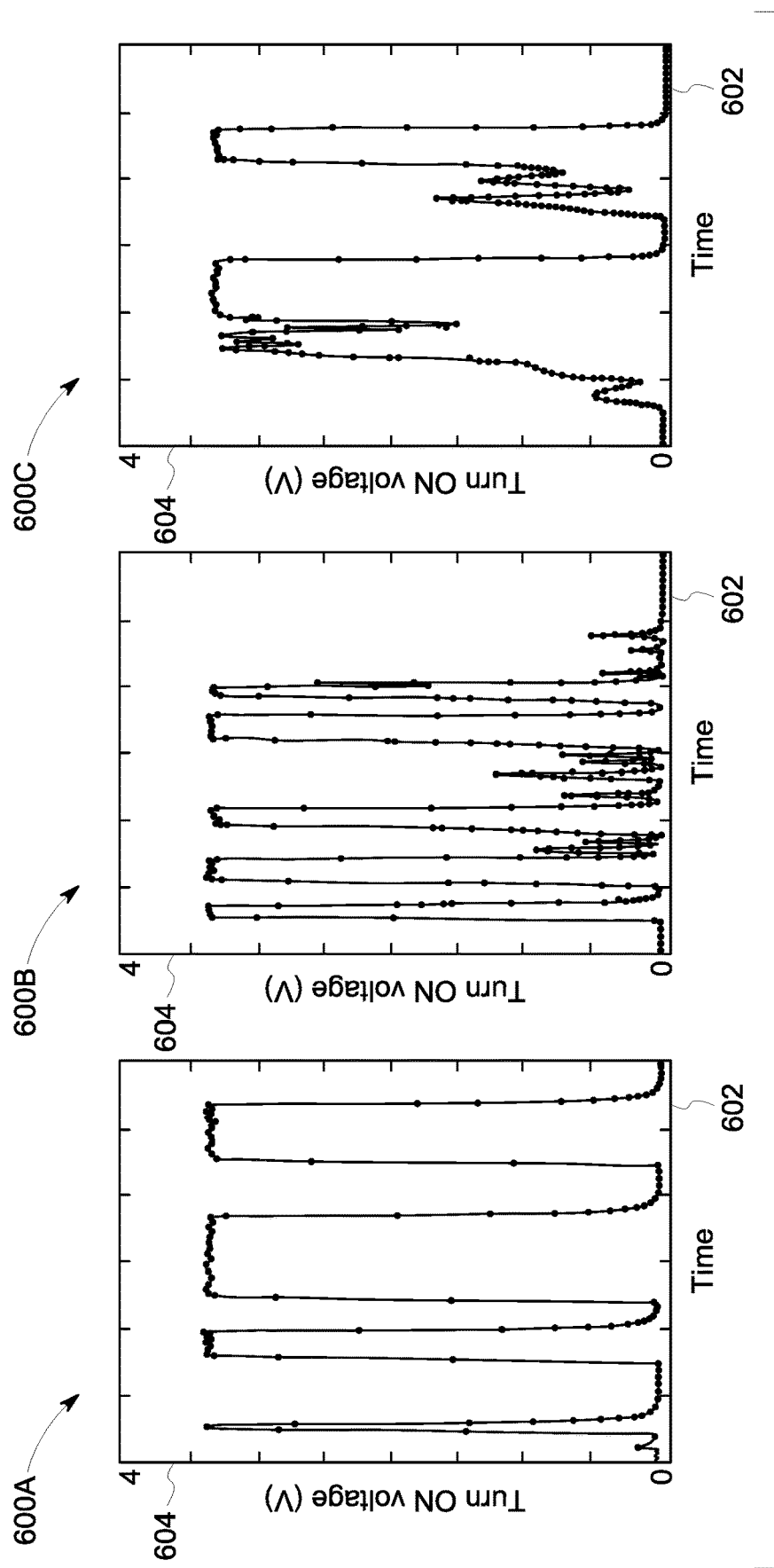
FIG. 6 illustrates graphical illustrations of voltage responses of a transducer of a sensor system in accordance with one embodiment.

FIG. 6 illustrates graphical illustrations of voltage responses of one of the transducers of the sensor system 100 in accordance with one embodiment. The graphs 600A, 600B, 600C are indicative of responses of one of the transducers of the circuit system 102 to different levels of a model gas to different sensing materials. For example, graph 500A may be a voltage response of a transducer having a polyaniline sensing film sensing material, graph 500B may be a voltage response of a transducer having a ionic polymer sensing film sensing material, and graph 500C may be a voltage response of a transducer having a metal oxide sensing film sensing material.

The electrical signals are shown alongside a horizontal axis 602 representative of time, and a vertical axis 604 representative of magnitudes of voltage. The sensor system 100 was able to produce activation voltage of about 3.5 volts when different transducers having the different sensing materials were used.

Figure 7:
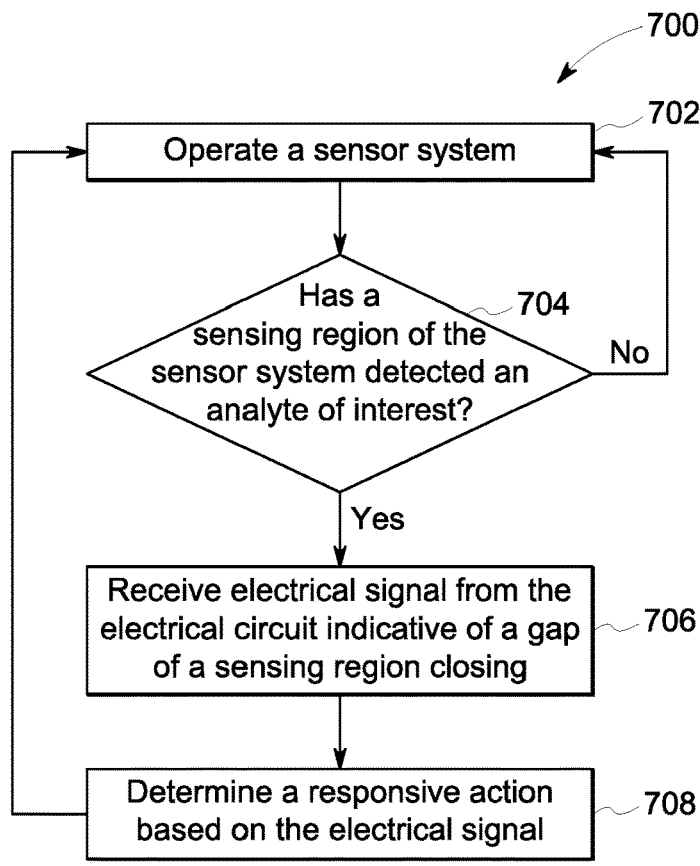
FIG. 7 illustrates a flowchart of one embodiment of a method for event-triggered sensing in accordance with one embodiment.

FIG. 7 illustrates a flowchart of one embodiment of a method 700 for event-triggered sensing in accordance with one embodiment. The method 700 can represent operations performed by the sensor system 100 described herein, or optionally can represent the operations performed by another sensing system. For example, the method 700 can represent operations performed by the sensing system 100, the circuit system 102, and system controller 104 under direction of one or more software applications, or optionally can represent an algorithm useful for writing such software applications.

At 702, the sensor system 100 may be disposed in a geographical area, an industrial site, a building or facility, or the like, to operate. The sensor system 100 may be in a normal open position (e.g., in an initial zero-power, standby-mode, off-mode, or the like) such that the electrical circuit 108 is open and no electric current is conducted through the electrical circuit 108. At 704, if one or more sensing regions have detected one or more analytes of interest, flow of the method proceeds to 706. Alternatively, if the one or more sensing regions do not detect an analyte of interest, flow of the method returns to 702. Responsive to one of the sensing regions detecting an analyte of interest, one or more gaps of the sensing region may close. Closing the one or more gaps changes the state of the sensor system 100 from the normal open position (e.g., initial zero-power, standby-mode, off-mode, of the like) to a closed position (e.g., on-mode, active-mode, or the like) such that the electrical circuit 108 is closed and electric current can be conducted through the electrical circuit 108. The sensor system 100 in the closed position consumes an increased amount of power relative to the sensor system 100 in the open position.

At 706, one or more processors of a system controller 104 receives one or more electrical signals from the electrical circuit 108 indicative of one or more gaps of one or more sensing regions closing. The electrical signal may include one or more properties of the closed electrical circuit 108 (e.g., voltage, electric current, or the like) and/or may indicate an identity of the one or more analyte of interests that were detected by the sensing region, an amount of the analyte of interest, a time stamp of when the analyte of interest was detected, a time stamp of when the amount of the analyte of interest met and/or exceeded an upper limit or lower limit predetermined threshold, or the like. The closing of the one or more gaps of one or more sensing regions can be related to different responses of real and/or imaginary parts of the complex permittivity to different analyte species.

At 708, one or more processors of the system controller 104 may determine a responsive action of a user or subject (e.g., human, animal, or the like) of the sensor system 100, a responsive action of an asset of the user of the sensor system, or the like. The subject may be one or more individuals in industries such as, but not limited to, industrial, educational, law-enforcement, entertainment, security, safety, military, or any other workers or user. The asset may be an industrial asset such as oil fluid reservoirs, associated piping components, connectors, flow-through components, or any other relevant industrial or process components. Optionally, the asset may be an airplane, locomotive, truck, passenger car, a home appliance, a sport equipment asset, military system, or the like.

The one or more processors can determine a responsive action of the subject or user, and/or a responsive action of the asset of the user. For example, the responsive action may include one or more of displaying of the detected analyte of interest, displaying or communicating a level of change of a parameter of the sensor system 100, sounding an alarm, transferring data to a remote location, guidance of the subject to change physical activity and/or locations, guidance of the subject to change environmental conditions around, proximate to, or in operational contact with the subject, directing the subject to ventilate the area the contains the sensor system 100, evacuation of the subject, changing a control state of the asset in operational contact with the subject, changing a maintenance schedule of the asset, or the like.

In one or more embodiments, responsive to one or more of the sensing regions detecting one or more analytes of interest, the electrical circuit 108 and/or the system controller 104 can activate one or more other sensor systems, communicate with a central station (e.g., the central station 120), communicate with one or more other sensors (not shown), communicate with one or more other sensor systems (not shown), change one or more operating parameters of the sensor system 100, begin data logging with the electrical circuit 108 and/or with the system controller 104, start data trending with the electrical circuit 108 and/or the system controller 104, or the like.

Figure 8:
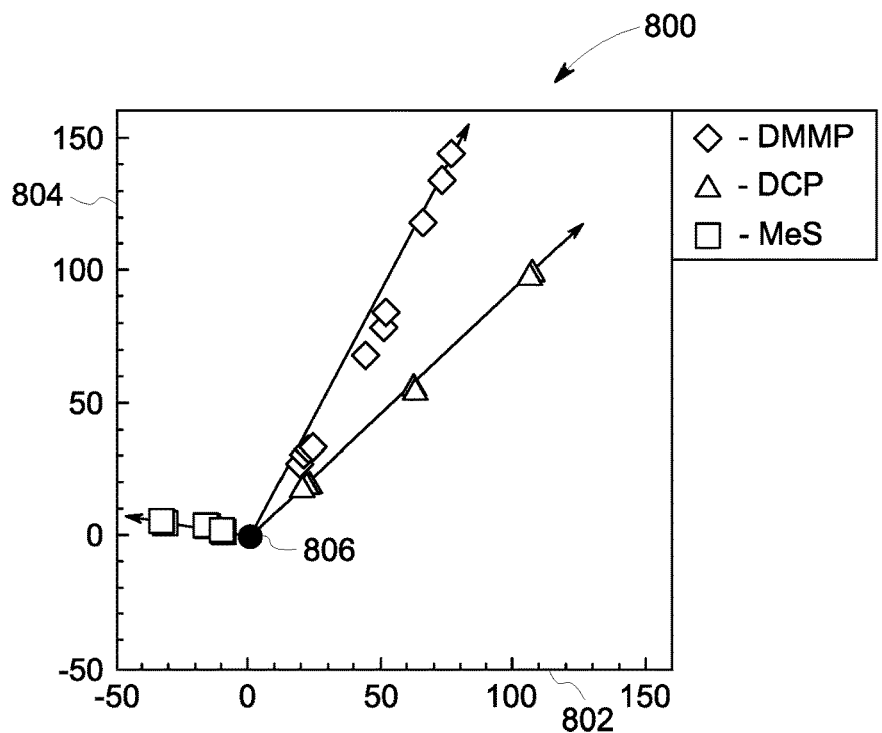
FIG. 8 illustrates a graphical depiction of changes of real and imaginary parts of a complex permittivity of a sensing material to different analyte species in accordance with one embodiment.

FIG. 8 illustrates a graphical depiction of changes of real and imaginary parts of the complex permittivity of a sensing material to different analyte species in accordance with one embodiment. A graph 800 includes a horizontal axis 802 representative of relative units of a change in the real part of the complex permittivity, and a vertical axis 804 representative of relative units of a change in the imaginary part of the complex permittivity. As one example, in order to obtain the graph 800, a sensing material in a form of ligand-functionalized gold nanoparticles was used and was applied onto an interdigital electrode structure. The graph 800 includes a reference gas, such as a clean carrier gas 806 that has a substantially zero change in the real part and substantially zero change in the imaginary part of the complex permittivity. For example, the clean carrier gas 806 may represent a baseline gas. Three model analyte volatiles were used such as chemical warfare agent (CWA) simulants. The model analyte volatiles were Methyl salicylate (MeS), 1,5-dichloropentane (DCP), and Dimethyl methylphosphonate (DMMP) and were presented to the sensor at different concentrations. As shown in FIG. 8, the relationship between the real part and the imaginary parts of the complex permittivity for each individual analyte was specific and provided clean and unique directions of the sensor response for each analyte.

In one or more embodiments of the subject matter described herein, a sensor system includes an electrical circuit having plural leads operably coupled with one or more sensing regions. One or more of the sensing regions includes a gap having a sensing material. The sensing material of each of the sensing regions is configured to detect an analyte of interest. One or more of the gaps is configured to close responsive to the sensing material corresponding to the one or more gaps detecting the analyte of interest. The sensor system also includes one or more processors communicatively coupled with the electrical circuit. The one or more processors receive one or more electrical signals from the electrical circuit indicative of one or more of the gaps closing responsive to the sensing material of the corresponding gaps detecting the analyte of interest. The electrical circuit is in a closed position in the presence of the analyte of interest. The sensor system is configured to consume an increased amount of power when the electrical circuit is in the closed position relative to the electrical circuit in an open position responsive to the one or more of the gaps closing. The one or more processors are configured to determine a responsive action based on the one or more electrical signals.

Optionally, the electrical circuit is configured to change between the open position and the closed position. The open position indicative of an absence of the analyte of interest, and the closed position indicative of the presence of the analyte of interest.

Optionally, the electrical circuit is in the closed position responsive to a number of the gaps of the sensing regions closing exceeding a predetermined threshold.

Optionally, the one or more electrical signals includes an identify of the analyte of interest.

Optionally, the one or more gaps are configured to close responsive to a relationship between a real part of a complex permittivity of the sensing material and an imaginary part of the complex permittivity of the sensing material exceeding at least one predetermined threshold.

Optionally, the gap of a first sensing region is configured to close responsive to the sensing material of the first sensing region detecting a first analyte of interest, and the gap of the first sensing region is configured to open responsive to the sensing material of the first sensing region detecting a different, second analyte of interest.

Optionally, one or more properties of the sensing material is configured to change responsive to the sensing material detecting the analyte of interest.

Optionally, the gap is a non-conductive gap substantially filled with the sensing material.

Optionally, the responsive action includes one or more responsive actions of a user of the sensor system or an asset of the user of the sensor system.

Optionally, the sensing material of one or more of the sensing regions is a multi-response sensing material configured to respond to different analytes of interest.

Optionally, the electrical circuit is configured to one or more of activate one or more other sensor systems, communicate with a central station, communicate with one or more other sensors, communicate with the one or more other sensor systems, change one or more operating parameters of the sensor system, start data logging with the electrical circuit, or start data trending with the electrical circuit.

In another embodiment of the subject matter described herein, a method includes detecting an analyte of interest with sensing material of one or more sensing regions of an electrical circuit of a sensor system. One or more of the sensing regions includes a gap comprising the sensing material. One or more of the gaps are configured to close responsive to the sensing material corresponding to the one or more gaps detecting the analyte of interest. The sensor system is configured to consume an increased amount of power when the electrical circuit is in a closed position relative to the electrical circuit in an open position responsive to the one or more of the gaps closing. One or more electrical signals are received from the electrical circuit indicative of one or more of the gaps closing responsive to the sensing material of the corresponding gaps detecting the analyte of interest. A responsive action is determined based on the one or more electrical signals.

Optionally, the electrical circuit changes between the open position and the closed position. The open position indicative of an absence of the analyte of interest, and the closed position indicative of the presence of the analyte of interest.

Optionally, the electrically circuit is in the closed position response to a number of the gaps of the sensing regions closing exceeding a predetermined threshold.

Optionally, the predetermined threshold is configured to be adaptable based on one or more external inputs to the sensor system.

Optionally, the one or more electrical signals includes an identity of the analyte of interest.

Optionally, the one or more gaps closes responsive to a relationship between a real part of a complex permittivity of the sensing material and an imaginary part of the complex permittivity of the sensing material exceeding a predetermined threshold.

Optionally, the gap of a first sensing region closes responsive to the sensing material of the first sensing region detecting a first analyte of interest, and opens responsive to the sensing material of the first sensing region detecting a different, second analyte of interest.

Optionally, one or more properties of the sensing material is configured to change responsive to the sensing material detecting the analyte of interest.

Optionally, one or more of the gaps is a non-conductive gap substantially filled with the sensing material.

Optionally, the responsive action includes one or more responsive actions of a user of the sensor system or an asset of the user of the sensor system.

Optionally, the sensing material of one or more of the sensing regions is a multi-response sensing material configured to respond to different analytes of interest.

Optionally, the method also includes one or more of activating one or more other sensor systems, communicating with a central station, communicating with one or more other sensors, communicating with the one or more other sensor systems, changing one or more operating parameters of the sensor system, starting data logging with the electrical circuit, or starting data trending with the electrical circuit.

In another embodiment of the subject matter described herein, a sensor system includes an electrical circuit comprising plural leads operably coupled with one or more sensing regions. One or more of the sensing regions includes a gap comprising a sensing material. The sensing material of each of the sensing regions is configured to detect an analyte of interest. One or more of the gaps are configured to close responsive to the sensing material corresponding to the gaps detecting the analyte of interest. One or more processors are communicatively coupled with the electrical circuit. The one or more processors are configured to receive one or more electrical signals from the electrical circuit indicative of one or more of the gaps closing responsive to the sensing material of the corresponding gaps detecting the analyte of interest. The one or more gaps are configured to close responsive to a ratio between a real part of a complex permittivity of the sensing material and an imaginary part of the complex permittivity of the sensing material exceeding at least one predetermined threshold. The one or more processors are configured to determine a responsive action based one the one or more electrical signals.

In another embodiment of the subject matter described herein, a method includes detecting an analyte of interest with sensing material of one or more sensing regions of an electrical circuit of a sensor system. One or more of the sensing regions includes a gap comprising the sensing material. One or more of the gaps are configured to close responsive to the sensing material corresponding to the gaps detecting the analyte of interest. The one or more gaps are configured to close responsive to a relationship between a real part of a complex permittivity of the sensing material and an imaginary part of the complex permittivity of the sensing material exceeding a predetermined threshold. One or more electrical signals are received from the electrical circuit indicative of one or more of the gaps closing responsive to the sensing material of the corresponding gaps detecting the analyte of interest. A responsive action is determined based on the one or more electrical signals.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor system comprising:
   an electrical circuit comprising plural leads operably coupled with one or more sensing regions, one or more of the sensing regions comprising a sensing material, wherein the sensing material of each of the sensing regions is configured to detect an analyte of interest, and wherein the electrical circuit is configured to, in response to the sensing material detecting the analyte of interest, become electrically conductive based on a relationship between a real part of a complex permittivity of the sensing material and an imaginary part of the complex permittivity of the sensing material exceeding at least one predetermined threshold; and
   one or more processors communicatively coupled with the electrical circuit, the one or more processors configured to receive one or more electrical signals from the electrical circuit indicative of the sensing material detecting the analyte of interest,
   wherein the electrical circuit is in an electrically closed position in the presence of the analyte of interest, wherein the sensor system is configured to consume an increased amount of power when the electrical circuit is in the electrically closed position relative to the electrical circuit in an electrically open position, and
   wherein the one or more processors are configured to determine a responsive action based on the one or more electrical signals.

2. The sensor system of claim 1, wherein the electrical circuit is configured to change between the electrically open position and the electrically closed position, the electrically open position indicative of an absence of the analyte of interest, and the electrically closed position indicative of the presence of the analyte of interest.

3. The sensor system of claim 1, wherein the electrical circuit is in the electrically closed position responsive to a number of the sensing regions closing exceeding a predetermined threshold.

4. The sensor system of claim 1, wherein the one or more electrical signals includes an identity of the analyte of interest.

5. The sensor system of claim 1, wherein of a first sensing region is configured to electrically close responsive to the sensing material of the first sensing region detecting a first analyte of interest, and wherein the first sensing region is configured to electrically open responsive to the sensing material of the first sensing region detecting a different, second analyte of interest.

6. The sensor system of claim 1, wherein one or more properties of the sensing material is configured to change responsive to the sensing material detecting the analyte of interest.

7. The sensor system of claim 1, wherein one or more of the sensing regions comprise a non-conductive gap substantially filled with the sensing material.

8. The sensor system of claim 1, wherein the responsive action includes one or more responsive actions of a user of the sensor system.

9. The sensor system of claim 1, wherein the sensing material of one or more of the sensing regions is a multi-response sensing material configured to respond to different analytes of interest.

10. The sensor system of claim 1, wherein the electrical circuit is configured to one or more of activate one or more other sensor systems, communicate with a central station, communicate with one or more other sensors, communicate with the one or more other sensor systems, change one or more operating parameters of the sensor system, start data logging with the electrical circuit, or start data trending with the electrical circuit.

11. A method comprising:
    detecting an analyte of interest with sensing material of one or more sensing regions of an electrical circuit of a sensor system, one or more of the sensing regions comprising the sensing material, wherein the electrical circuit is configured to, in response to the sensing material detecting the analyte of interest, become electrically conductive based on a relationship between a real part of a complex permittivity of the sensing material and an imaginary part of the complex permittivity of the sensing material exceeding a predetermined threshold, wherein the sensor system is configured to consume an increased amount of power when the electrical circuit is in an electrically closed position relative to the electrical circuit in an electrically open position;
    receiving one or more electrical signals from the electrical circuit indicative of the sensing material detecting the analyte of interest; and
    determining a responsive action based on the one or more electrical signals.

12. The method of claim 11, further comprising changing the electrical circuit between the open position and the electrically closed position, the electrically open position indicative of an absence of the analyte of interest, and the electrically closed position indicative of the presence of the analyte of interest.

13. The method of claim 11, wherein the electrical circuit is in the electrically closed position responsive to a number of the sensing regions electrically closing exceeding a predetermined threshold.

14. The method of claim 13, wherein the predetermined threshold is configured to be adaptable based on one or more external inputs to the sensor system.

15. The method of claim 11, wherein the one or more electrical signals includes an identity of the analyte of interest.

16. The method of claim 11, further comprising electrically closing a first sensing region responsive to the sensing material of the first sensing region detecting a first analyte of interest, and electrically opening the first sensing region responsive to the sensing material of the first sensing region detecting a different, second analyte of interest.

17. The method of claim 11, wherein one or more properties of the sensing material is configured to change responsive to the sensing material detecting the analyte of interest.

18. The method of claim 11, wherein one or more of the sensing regions include a non-conductive gap substantially filled with the sensing material.

19. The method of claim 11, wherein the responsive action includes one or more responsive actions of a user of the sensor system.

20. The method of claim 11, wherein the sensing material of one or more of the sensing regions is a multi-response sensing material configured to respond to different analytes of interest.

21. The method of claim 11, further comprising one or more of activating one or more other sensor systems, communicating with a central station, communicating with one or more other sensors, communicating with the one or more other sensor systems, changing one or more operating parameters of the sensor system, starting data logging with the electrical circuit, or starting data trending with the electrical circuit.

22. A sensor system comprising:
an electrical circuit comprising plural leads operably coupled with one or more sensing regions, one or more of the sensing regions comprising a sensing material, wherein the sensing material of each of the sensing regions is configured to detect an analyte of interest; and
one or more processors communicatively coupled with the electrical circuit, the one or more processors configured to receive one or more electrical signals from the electrical circuit responsive to the sensing material detecting the analyte of interest,
wherein the electrical circuit is configured to electrically close responsive to a ratio between a real part of a complex permittivity of the sensing material and an imaginary part of the complex permittivity of the sensing material exceeding at least one predetermined threshold; and
wherein the one or more processors are configured to determine a responsive action based on the one or more electrical signals.

23. A method comprising:
detecting an analyte of interest with sensing material of one or more sensing regions of an electrical circuit of a sensor system, wherein the electrical circuit is configured to electrically close responsive to the sensing material detecting the analyte of interest, wherein the electrical circuit is configured to close electrically responsive to a relationship between a real part of a complex permittivity of the sensing material and an imaginary part of the complex permittivity of the sensing material exceeding a predetermined threshold;
receiving one or more electrical signals from the electrical circuit indicative of the electrical circuit electrically closing responsive to the sensing material detecting the analyte of interest; and
determining a responsive action based on the one or more electrical signals.

\* \* \* \* \*